(12) United States Patent
Fujisawa et al.

(10) Patent No.: US 12,303,187 B2
(45) Date of Patent: May 20, 2025

(54) MEDICAL IMAGE PROCESSING APPARATUS

(71) Applicant: CANON MEDICAL SYSTEMS CORPORATION, Otawara (JP)

(72) Inventors: Yasuko Fujisawa, Nasushiobara (JP); Shintaro Funabasama, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 958 days.

(21) Appl. No.: 17/101,254

(22) Filed: Nov. 23, 2020

(65) Prior Publication Data

US 2021/0161588 A1 Jun. 3, 2021

(30) Foreign Application Priority Data

Nov. 29, 2019 (JP) ................................ 2019-217382
Nov. 29, 2019 (JP) ................................ 2019-217383

(51) Int. Cl.
*A61B 18/14* (2006.01)
*G06F 3/14* (2006.01)
(Continued)

(52) U.S. Cl.
CPC ............ *A61B 18/1477* (2013.01); *G06F 3/14* (2013.01); *G06T 7/0014* (2013.01);
(Continued)

(58) Field of Classification Search
CPC ................ A61B 18/1477; A61B 6/032; A61B 2017/00119; A61B 2018/00577;
(Continued)

(56) References Cited

U.S. PATENT DOCUMENTS 7,817,828 B2    10/2010   Miyazaki et al.
8,306,629 B2 *   11/2012   Mioduski ........... A61B 18/1233
                                                           607/101
(Continued)

FOREIGN PATENT DOCUMENTS

JP         2-291837 A     12/1990
JP     2009-233043 A     10/2009
(Continued)

OTHER PUBLICATIONS

Japanese Office Action issued on May 9, 2023 in Japanese Patent Application No. 2019-217383, 3 pages.
Japanese Office Action issued on May 16, 2023 in Japanese Patent Application No. 2019-217382, 2 pages.
Japanese Office Action issued Oct. 3, 2023 in Japanese Patent Application No. 2019-217382, 2 pages.

*Primary Examiner* — Pascal M Bui Pho
*Assistant Examiner* — Michael Yiming Fang
(74) *Attorney, Agent, or Firm* — Oblon, McClelland, Maier & Neustadt, L.L.P.

(57) ABSTRACT

A medical image processing apparatus according to a first embodiment includes processing circuitry. The processing circuitry is configured to generate information related to temperature by using a first image obtained by imaging one or more observation regions prior to treatment and at least one second image obtained by imaging the one or more observation regions during the treatment, generate alert information on a basis of the information related to temperature, and cause a display to output the alert information together with the information related to temperature.

21 Claims, 9 Drawing Sheets

(51) Int. Cl.
*G06T 7/00* (2017.01)
*G06T 11/00* (2006.01)
*G06T 11/20* (2006.01)
*A61B 6/03* (2006.01)
*A61B 17/00* (2006.01)
*A61B 18/00* (2006.01)

(52) U.S. Cl.
CPC .......... *G06T 11/001* (2013.01); *G06T 11/203* (2013.01); *A61B 6/032* (2013.01); *A61B 2017/00119* (2013.01); *A61B 2018/00577* (2013.01); *A61B 2018/00791* (2013.01); *A61B 2018/00898* (2013.01); *A61B 2018/00982* (2013.01); *A61B 2018/1425* (2013.01); *G06T 2207/30004* (2013.01); *G06V 2201/03* (2022.01)

(58) Field of Classification Search
CPC .......... A61B 2018/00791; A61B 2018/00898; A61B 2018/00982; A61B 2018/1425; A61B 18/08; A61B 2018/00797; A61B 2018/00821; A61B 2018/00803; A61B 2018/00815; A61B 2018/00642; A61B 2018/00708; A61B 2090/3762; A61B 90/37; A61B 18/02; A61B 18/18; G06V 2201/03; G06V 2201/031; G06F 3/14; G06T 7/0014; G06T 11/001; G06T 11/203; G06T 2207/30004; G09G 2380/08
See application file for complete search history.

(56) References Cited

U.S. PATENT DOCUMENTS

| | | | |
|---|---|---|---|
| 9,393,071 B1* | 7/2016 | Boveja | A61B 18/1492 |
| 10,743,773 B2 | 8/2020 | Abi-Jaoudeh et al. | |
| 2005/0171583 A1* | 8/2005 | Mosher | A61B 17/0625 |
| | | | 607/113 |
| 2007/0239062 A1* | 10/2007 | Chopra | A61B 5/4381 |
| | | | 600/549 |
| 2008/0027314 A1 | 1/2008 | Miyazaki et al. | |
| 2009/0262980 A1* | 10/2009 | Markowitz | A61B 5/287 |
| | | | 382/128 |
| 2013/0184697 A1* | 7/2013 | Han | A61B 90/37 |
| | | | 606/32 |
| 2015/0038883 A1* | 2/2015 | Kurtz | G01R 33/4814 |
| | | | 601/3 |
| 2015/0150466 A1 | 6/2015 | Abi-Jaoudeh et al. | |
| 2017/0027639 A1 | 2/2017 | Margallo et al. | |
| 2018/0235509 A1* | 8/2018 | Doron | A61B 5/287 |
| 2019/0159823 A1* | 5/2019 | Yang | G16H 40/63 |
| 2019/0247130 A1* | 8/2019 | State | A61B 34/20 |
| 2020/0391019 A1* | 12/2020 | Levy | A61B 8/481 |
| 2021/0093897 A1* | 4/2021 | Zadicario | A61B 8/5261 |
| 2021/0186594 A1* | 6/2021 | Tanigami | A61B 18/148 |
| 2021/0205016 A1* | 7/2021 | Safraoui | A61B 18/203 |
| 2022/0079677 A1* | 3/2022 | Hautvast | A61B 18/1233 |

FOREIGN PATENT DOCUMENTS

| | | |
|---|---|---|
| JP | 2015-517324 A | 6/2015 |
| JP | 2018-524124 A | 8/2018 |
| WO | WO 2005/039416 A1 | 5/2005 |

* cited by examiner

MEDICAL IMAGE PROCESSING APPARATUS

CROSS-REFERENCE TO RELATED APPLICATIONS

This application is based upon and claims the benefit of priority from Japanese Patent Applications No. 2019-217382 and No. 2019-217383, both filed on Nov. 29, 2019, the entire contents of all of which are incorporated herein by reference.

FIELD

Embodiments described herein relate generally to a medical image processing apparatus.

BACKGROUND

In recent years, as a type of cancer treatment, a treatment method has become widespread by which radio ablation is performed under guidance of Computed Tomography (CT). Ablation denotes a treatment method by which, for example, cancer cells are ablated and destructed with radio waves, by inserting an ablation needle (an electrode needle or a puncture needle) in the cancer cells and applying a radio frequency thereto.

Conventionally, when such an ablation treatment is performed, there has been a desire to monitor whether a target temperature is reached or not by using thermography or by inserting a needle to which a thermometer is attached into the cancer cells subject to the ablation.

However, thermography is designed to take the temperature on the body surface of the examined subject. Accordingly, during the ablation treatment, it is not possible to know, for example, the present temperature of the ablation target inside the body of the examined subject (hereinafter, "patient") or whether or not the ablation target has reached a temperature equal to or higher than a target temperature (e.g., 70 centigrade) to destruct the cancer cells. For this reason, it is difficult for practitioners to judge, in a real-time manner, at which point the manipulation should be stopped and to what extent the impact of the heat has been exerted.

Further, as for the method by which the temperature inside the patient's body is taken by inserting a needle to which a thermometer is attached, it is tremendously troublesome for practitioners to take the temperature during the treatment by using this method. In addition, because the number of puncture locations increases, a burden is imposed on the patient.

DETAILED DESCRIPTION

Exemplary embodiments of a medical image processing apparatus will be explained below in detail, with reference to the accompanying drawings.

First Embodiment

A medical image processing apparatus according to a first embodiment includes processing circuitry. The processing circuitry is configured to generate information related to temperature by using a first image obtained by imaging one or more observation regions prior to treatment and at least one second image obtained by imaging the one or more observation regions during the treatment, generate alert information on a basis of the information related to temperature, and cause a display to output the alert information together with the information related to temperature.

Figure 1:
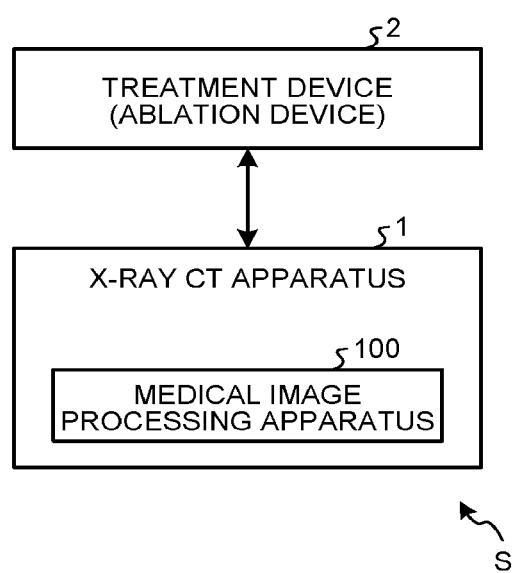
FIG. 1 is a diagram illustrating an exemplary configuration of a treatment system S using a medical image processing apparatus according to a first embodiment.

FIG. 1 is a diagram illustrating a configuration of a treatment system S using a medical image processing apparatus 100 according to a first embodiment. As illustrated in FIG. 1, the treatment system S includes an X-ray Computed Tomography apparatus 1 (hereinafter, "X-ray CT apparatus 1") and a treatment device 2. In the present embodiment, the X-ray CT apparatus 1 and the treatment device 2 are capable of communicating each other; however, the communication capability is optional.

The treatment device 2 is a treatment device configured to destruct cancer cells by inserting a needle into a tissue of a patient and, from the needle, supplying heat, energy, a wave, or the like for the purpose of implementing ablation using a radio wave, ablation using a microwave, or freezing using cryo, for example.

In the present embodiment, to provide specific explanations, the treatment device 2 is assumed to be an ablation device configured to perform ablation using a radio wave. (The treatment device 2 may hereinafter be referred to as "ablation device 2".) Further, in the present embodiment, within the patient's body, a region of a tumor subject to the ablation performed by the ablation device 2 and a region (hereinafter, "additional ablation region") subject to the ablation being added as a margin in the surroundings of the tumor region will together be referred to as an "ablation target region". A region (e.g., a blood vessel or the like) that is positioned in the surroundings of the ablation target region and needs to be spared from the ablation will be referred to as an "ablation avoidance region". Two or more additional ablation regions and/or two or more ablation avoidance regions may be set. Further, a region (e.g., the additional ablation region, the ablation avoidance region) that needs to be monitored by a practitioner during the treatment using the ablation will be referred to as an "observation region".

The X-ray CT apparatus 1 is a medical image diagnosis apparatus configured to obtain, in a real-time manner, CT images used for monitoring the position of the ablation needle in the patient's body and the observation region, during the treatment using the ablation device 2. In other words, during the treatment using the ablation device 2, the X-ray CT apparatus 1 is configured to obtain volume data related to the patient by implementing CT fluoroscopy, in response to instructions from the practitioner. The CT image data may be obtained through the CT fluoroscopy by performing either volume imaging or helical imaging.

Further, the X-ray CT apparatus 1 has the medical image processing apparatus 100 built therein. During the treatment using the ablation device 2, the medical image processing apparatus 100 is configured to generate and display information related to temperature regarding the observation region positioned in the patient's body, by using CT image data obtained by the X-ray CT apparatus 1. A configuration of the medical image processing apparatus 100 will be explained in detail later.

Figure 2:
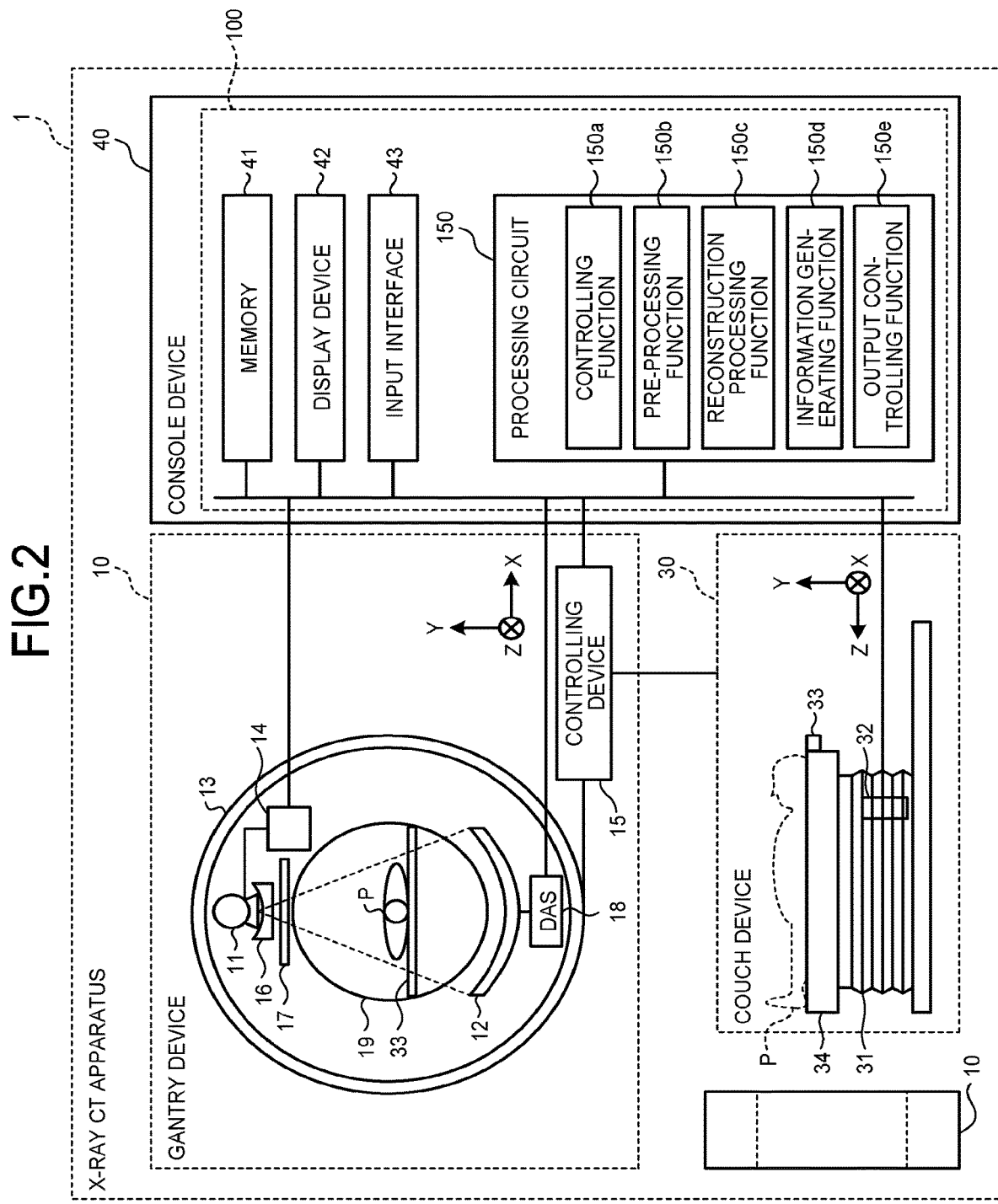
FIG. 2 is a block diagram illustrating an exemplary configuration of an X-ray CT apparatus according to the first embodiment.

Next, an outline of a configuration of the X-ray CT apparatus 1 will be explained. FIG. 2 is a block diagram illustrating an exemplary configuration of the X-ray CT apparatus 1 according to an embodiment. As illustrated in FIG. 2, the X-ray CT apparatus 1 according to the embodiment includes a gantry device 10, a couch device 30, and a console device 40.

In the present embodiment, the rotation axis of a rotating frame 13 in a non-tilted state or the longitudinal direction of a couchtop 33 of the couch device 30 is defined as a Z-axis direction; the axial direction orthogonal to the Z-axis direction and parallel to the floor surface is defined as an X-axis direction; and the axial direction orthogonal to the Z-axis direction and perpendicular to the floor surface is defined as a Y-axis direction.

The gantry device 10 includes an imaging system to take medical images used for diagnosing processes. In other words, the gantry device 10 is a device including the imaging system configured to radiate X-rays onto a patient P and to acquire projection data from detection data of X-rays that have passed through the patient P. The gantry device 10 includes an X-ray tube 11, a wedge 16, a collimator 17, an X-ray detector 12, an X-ray high-voltage device 14, a Data Acquisition System (DAS) 18, the rotating frame 13, a controlling device 15, and the couch device 30.

The X-ray tube 11 is a vacuum tube configured to emit thermo electrons from a negative pole (a filament) toward a positive pole (a target), with high voltage applied by the X-ray high-voltage device 14.

The wedge 16 is a filter used for adjusting the X-ray dose of the X-rays radiated from the X-ray tube 11. More specifically, the wedge 16 is a filter configured to pass and attenuate the X-rays radiated from the X-ray tube 11, so that the X-rays radiated from the X-ray tube 11 onto the patient P have a predetermined distribution.

For example, the wedge 16 may be a wedge filter or a bow-tie filter and is a filter obtained by processing aluminum so as to have a predetermined target angle and a predetermined thickness.

The collimator 17 is configured with lead plates or the like used for narrowing down the radiation range of the X-rays that have passed through the wedge 16 and is configured to form a slit with a combination of the plurality of lead plates or the like.

The X-ray detector 12 is configured to detect the X-rays that were radiated from the X-ray tube 11 and have passed through the patient P and to output an electrical signal corresponding to the amount of the X-rays to the data acquisition device (the DAS 18). The X-ray detector 12 includes, for example, a plurality of rows of X-ray detecting elements in each of which a plurality of X-ray detecting elements are arranged in a channel direction along an arc centered on a focal point of the X-ray tube 11. The X-ray detector 12 includes, for example, a plurality of rows of X-ray detecting elements in each of which a plurality of X-ray detecting elements are arranged in a channel direction along an arc centered on a focal point of the X-ray tube. For example, the X-ray detector 12 has a structure in which the plurality of rows of X-ray detecting elements are arranged in a slice direction (which may be called a body axis direction or a row direction), the plurality of rows each having the plurality of X-ray detecting elements arranged in the channel direction.

Further, the X-ray detector 12 is, for example, a detector of an indirect conversion type including a grid, a scintillator array, and an optical sensor array. The scintillator array includes a plurality of scintillators. Each of the scintillators includes a scintillator crystal that outputs light having a photon quantity corresponding to the amount of the X-rays that have become incident thereto. The grid is disposed on the surface of the scintillator array positioned on the X-ray incident side and includes an X-ray blocking plate having a function of absorbing scattered X-rays. The optical sensor array has a function of converting the light received from the scintillators into electrical signals corresponding to the quantity thereof and includes optical sensors such as photomultiplier tubes (PMTs) or the like. Alternatively, the X-ray detector 12 may be a detector of a direct conversion type including a semiconductor element configured to convert the incident X-rays into electrical signals.

The X-ray high-voltage device 14 includes a high-voltage generating device including electrical circuits such as a transformer, a rectifier, and the like and having a function of generating the high voltage to be applied to the X-ray tube 11; and an X-ray controlling device configured to control the output voltage in accordance with the X-rays radiated by the X-ray tube 11. The high-voltage generating device may be of a transformer type or of an inverter type. Further, the X-ray high-voltage device 14 may be provided for the rotating frame 13 or may be provided on the side of a fixed frame (not illustrated) of the gantry device 10. The fixed frame is a frame configured to rotatably support the rotating frame 13.

The DAS 18 includes: an amplifier configured to perform an amplifying process on the electrical signals output from the X-ray detecting elements of the X-ray detector 12; and an Analog/Digital (A/D) converter configured to convert the electrical signals into digital signals. The DAS 18 is configured to generate the detection data. The detection data generated by the DAS 18 is transferred to the console device 40.

The rotating frame 13 is an annular frame configured to support the X-ray tube 11 and the X-ray detector 12 so as to oppose each other and configured to rotate the X-ray tube 11 and the X-ray detector 12 via the controlling device 15. In addition to supporting the X-ray tube 11 and the X-ray detector 12, the rotating frame 13 may further support the X-ray high-voltage device 14 and the DAS 18. In an example, the detection data generated by the DAS 18 is transmitted from a transmitter including a light emitting diode and being provided on the rotating frame 13, to a receiver including a photodiode and being provided in a non-rotation part (e.g., the fixed frame) of the gantry device 10, through optical communication, and is further transferred to the console device 40. The method for transmitting the detection data from the rotating frame 13 to the non-rotation part of the gantry device 10 is not limited to optical communication and may be realized with any of other contactless data transfer methods.

The controlling device 15 includes: a processing circuit having a Central Processing Unit (CPU) or the like; and a driving mechanism configured with a motor, an actuator, and/or the like. Upon receipt of an input signal from an input interface 43 attached to the console device 40 or an input interface attached to the gantry device 10, the controlling device 15 has a function of controlling operations of the gantry device 10 and the couch device 30. Further, upon receipt of input signals, the controlling device 15 is configured to exercise control so as to rotate the rotating frame 13 and to bring the gantry device 10 and the couch device 30 into operation.

For example, the controlling device 15 tilts the gantry device 10 by rotating the rotating frame 13 on an axis parallel to the X-axis direction, on the basis of tilting angle (tilt angle) information input through an input interface attached to the gantry device 10. The controlling device 15 and a controlling function 150a included in a processing circuit 150 are examples of a controlling unit.

The couch device 30 is a device on which the patient P to be scanned is placed and which is configured to move the patient P. The couch device 30 includes a base 31, a couch driving device 32, the couchtop 33, and a supporting frame 34. The base 31 is a casing configured to support the supporting frame 34 so as to be movable in the vertical directions. The couch driving device 32 is a motor or an actuator configured to move the couchtop 33 on which the patient P is placed, along the long axis directions thereof (the Z-axis directions in FIG. 2). The couchtop 33 provided on the top face of the supporting frame 34 is a board on which the patient P is placed. In addition to the couchtop 33, the couch driving device 32 may also move the supporting frame 34 along the long axis directions of the couchtop 33.

According to control signals from the controlling device 15, the couch driving device 32 is configured to move the base 31 in up-and-down directions. According to control signals from the controlling device 15, the couch driving device 32 is configured to move the couchtop 33 in the long-axis directions.

The console device 40 is a device configured to receive operations performed by a user on the X-ray CT apparatus 1 and to also reconstruct X-ray CT image data from the X-ray detection data acquired by the gantry device 10. The console device 40 includes a memory 41, a display device 42, the input interface 43, and the processing circuit 150.

In this situation, the medical image processing apparatus 100 according to the present embodiment is realized, for example, by the memory 41, the display device 42, the input interface 43, and the processing circuit 150.

The memory 41 is realized by using a semiconductor memory element such as a Random Access Memory (RAM) or a flash memory, or a hard disk, an optical disk, or the like. For example, the memory 41 is configured to store therein the projection data and reconstructed image data. The memory 41 is an example of a storage unit.

Figure 3:
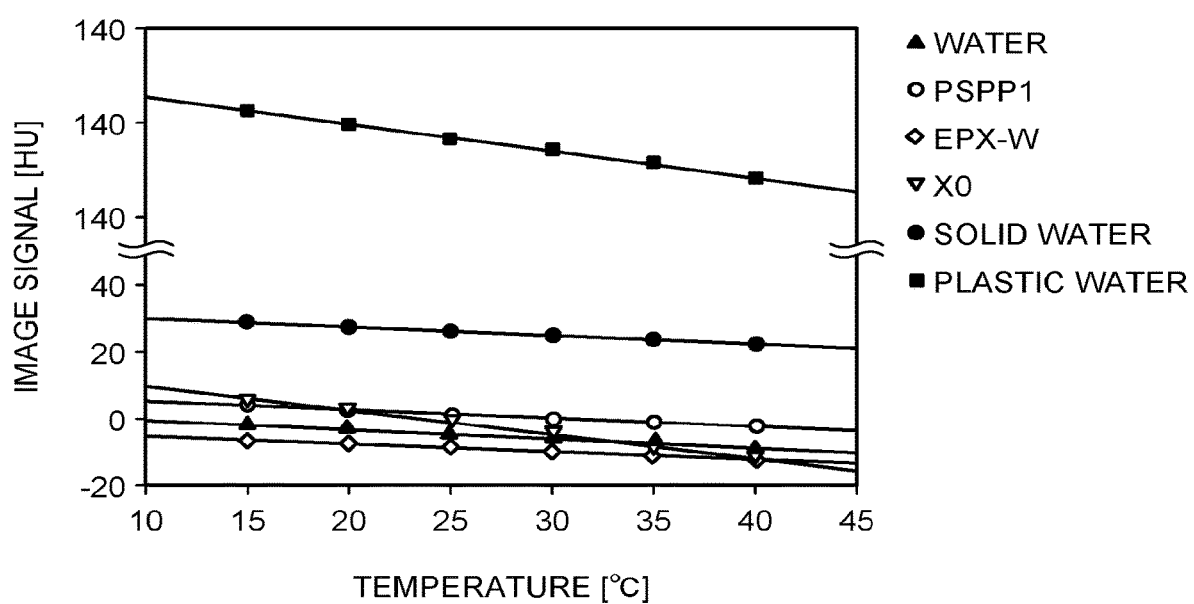
FIG. 3 is a chart illustrating an example of a graph indicating a correspondence relationship between CT value changes and temperature changes.

Further, the memory 41 stores therein a dedicated program for realizing the controlling function 150a, a pre-processing function 150b, a reconstruction processing function 150c, an information generating function 150d, and an output controlling function 150e (explained later). Further, the memory 41 stores therein information (graphs) each indicating a correspondence relationship between change amounts in a CT value (or change amounts in a pixel value kept in correspondence with the CT value) and change amounts in temperature as illustrated in FIG. 3; information (a table) related to temperature sensitivity of each tissue; information related to temperature generated by a process described below; and/or the like.

Returning to the description of FIG. 2, the display device 42 is a monitor referenced by the user and is configured to display various types of information. For example, the display device 42 is configured to output medical images (CT images) generated by the processing circuit 150, a Graphical User Interface (GUI) used for receiving various types of operations from the user, and the like. For example, the display device 42 is a liquid crystal display device or a Cathode Ray Tube (CRT) display device. The display device 42 is an example of the display unit.

The input interface 43 is configured to receive various types of input operations from the user, to convert the received input operations into electrical signals, and to output the electrical signals to the processing circuit 150. For example, the input interface 43 is configured to receive, from the user, an acquisition condition used at the time of acquiring the projection data, a reconstruction condition used at the time of reconstructing a CT images, an image processing condition used at the time of generating a post-processing image from the CT image, and the like. Further, for example, the input interface 43 is configured to receive inputs related to designating regions such as a tumor region, an ablation target region, and an ablation avoidance region. Further, for example, the input interface 43 is configured to receive an instruction to select information to be included in the alert information (explained later). For example, the input interface 43 is realized by using a mouse, a keyboard, a trackball, a switch, a button, a joystick, and/or the like. The input interface 43 is an example of an input unit.

The processing circuit 150 is configured to control operations of the entirety of the X-ray CT apparatus 1. For example, the processing circuit 150 includes the controlling function 150a, the pre-processing function 150b, the reconstruction processing function 150c, the information generating function 150d, and the output controlling function 150e. In an embodiment, processing functions performed by the constituent elements, namely, the controlling function 150a, the pre-processing function 150b, the reconstruction processing function 150c, the information generating function 150d, and the output controlling function 150e, are stored in the memory 41 in the form of computer-executable programs. The processing circuit 150 is a processor configured to realize the functions corresponding to the programs, by reading and executing the programs from the memory 41. In other words, the processing circuit 150 that has read the programs has the functions illustrated within the processing circuit 150 in FIG. 2.

With reference to FIG. 2, the example was explained in which the single processing circuit (the processing circuit 150) realizes the processing functions implemented by the controlling function 150a, the pre-processing function 150b, the reconstruction processing function 150c, the information generating function 150d, and the output controlling function 150e; however, it is also acceptable to structure the processing circuit 150 by combining together a plurality of independent processors, so that the functions are realized as a result of the processors executing the programs.

In other words, each of the functions described above may be configured as a program, so that the single processing circuit executes the programs. Alternatively, one or more specific functions may be installed in a dedicated and independent program executing circuit.

The term "processor" used in the above explanations denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 41. Alternatively, instead of saving the programs in the memory 41, it is also acceptable to directly incorporate the programs in the circuits of the one or more processors. In that situation, the one or more processors realize the functions by reading and executing the programs incorporated in the circuits thereof.

By employing the controlling function 150a, the processing circuit 150 is configured to control various types of functions of the processing circuit 150, on the basis of the input operations received from the user via the input interface 43. By employing the pre-processing function 150b, the processing circuit 150 is configured to generate data obtained by performing pre-processing processes such as a logarithmic conversion process, an offset process, an interchannel sensitivity correcting process, a beam hardening correction, and/or the like on the detection data output from the DAS 18. The data (the detection data) before the pre-processing processes and the data after the pre-processing processes may collectively be referred to as projection data. By employing the reconstruction processing function 150c, the processing circuit 150 is configured to generate the CT image data by performing a reconstructing process using a filtered back projection method, a successive approximation reconstruction method, or the like, on the projection data generated by the pre-processing function 150b. Further, by employing the reconstruction processing function 150c, the processing circuit 150 is configured to convert the reconstructed CT image data into tomography data or three-dimensional image data on an arbitrary cross-sectional plane, by using a publicly known method, on the basis of an input operation received from the user via the input interface 43.

By employing the information generating function 150d, the processing circuit 150 is configured to generate the information related to temperature regarding the observation region positioned in the patient's body, by using the CT image data obtained by the X-ray CT apparatus 1, during the treatment using the ablation device 2. In other words, by employing the information generating function 150d, the processing circuit 150 is configured to generate the information related to temperature, by using a CT image (the first image) obtained by imaging the observation region prior to the ablation manipulation while using the X-ray CT apparatus 1 and at least one CT image (the second image) obtained by imaging the observation region during the ablation manipulation while using the X-ray CT apparatus 1.

In this situation, the "information related to temperature" is, for example, information including at least one of: a temperature change map, a reached temperature map, an accumulated calories map, and a temperature change graph. Further, the "information related to temperature" includes information and the like generated on the basis of any of the temperature change map, the reached temperature map, the accumulated calories map, and the temperature change graph.

Next, the temperature change map, the reached temperature map, the accumulated calories map, and the temperature change graph will each be explained.

The temperature change map is information indicating a spatial distribution of the present temperature (or a temperature change amount from a reference temperature) in each of different positions in the observation region.

Figure 4:
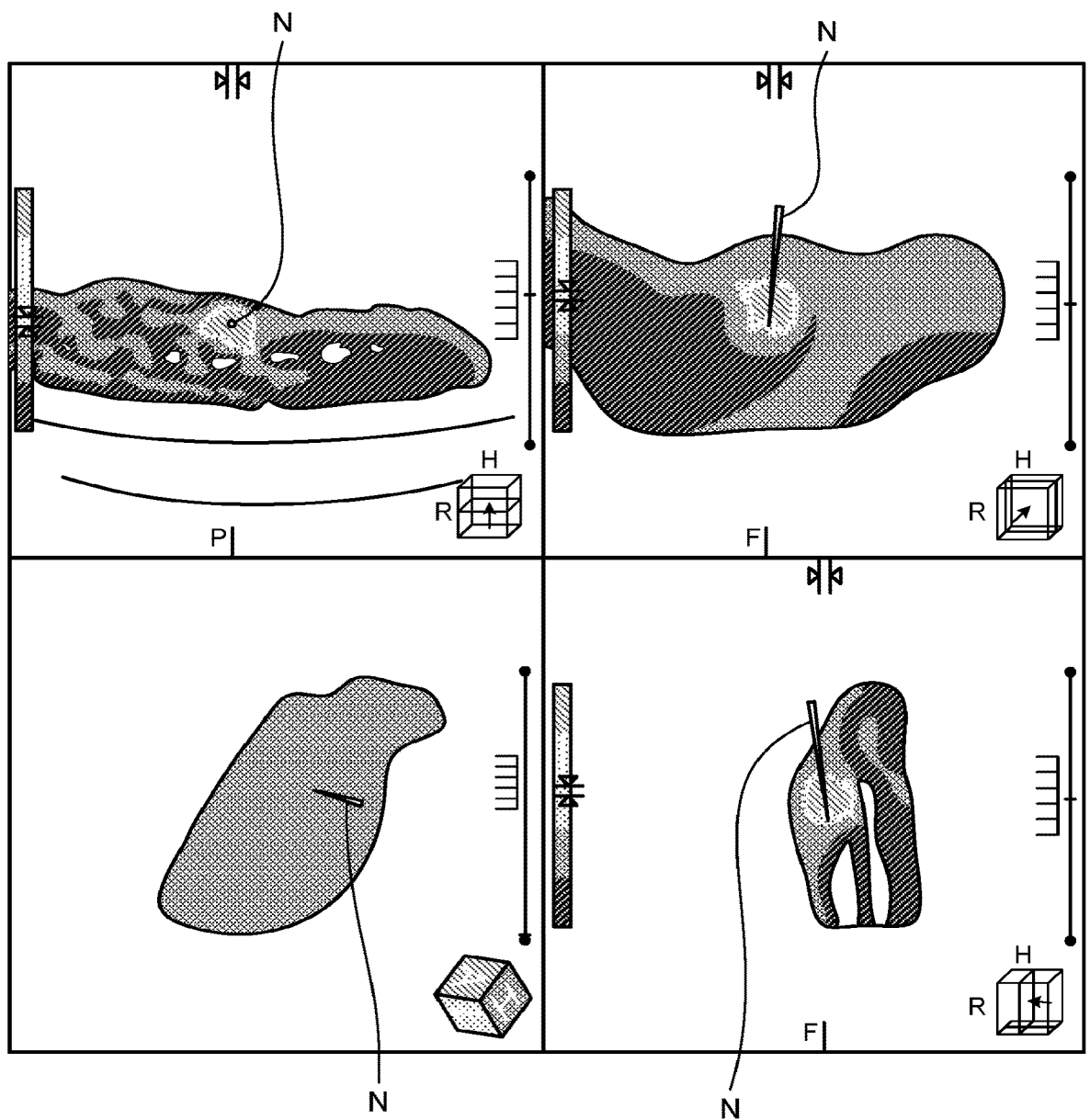
FIG. 4 is a drawing illustrating examples of temperature change maps.

FIG. 4 is a drawing illustrating examples of temperature change maps. In the example in FIG. 4, the observation region is set as the entirety of each of the images. In FIG. 4, a temperature change map on a coronal cross-sectional plane including an ablation needle N is at the top right; a temperature change map on a sagittal cross-sectional plane including the ablation needle N is at the bottom right; a temperature change map on an axial cross-sectional plane orthogonal to the ablation needle N is at the top left; and a volume rendering image serving as a three-dimensional image is at the bottom left. The temperature change maps are color maps each of which expresses differences in temperature as differences in color.

FIG. 4 illustrates the examples of the temperature change maps presented as the color maps. Alternatively, it is also acceptable to generate and display temperature change maps presented as a display of contour lines expressing differences in temperature by using isotherms, for example. When displaying the isotherms corresponding to temperature changes, it is possible to set a target temperature for destructing the cancer cells by using a scale (gradations).

Figure 5:
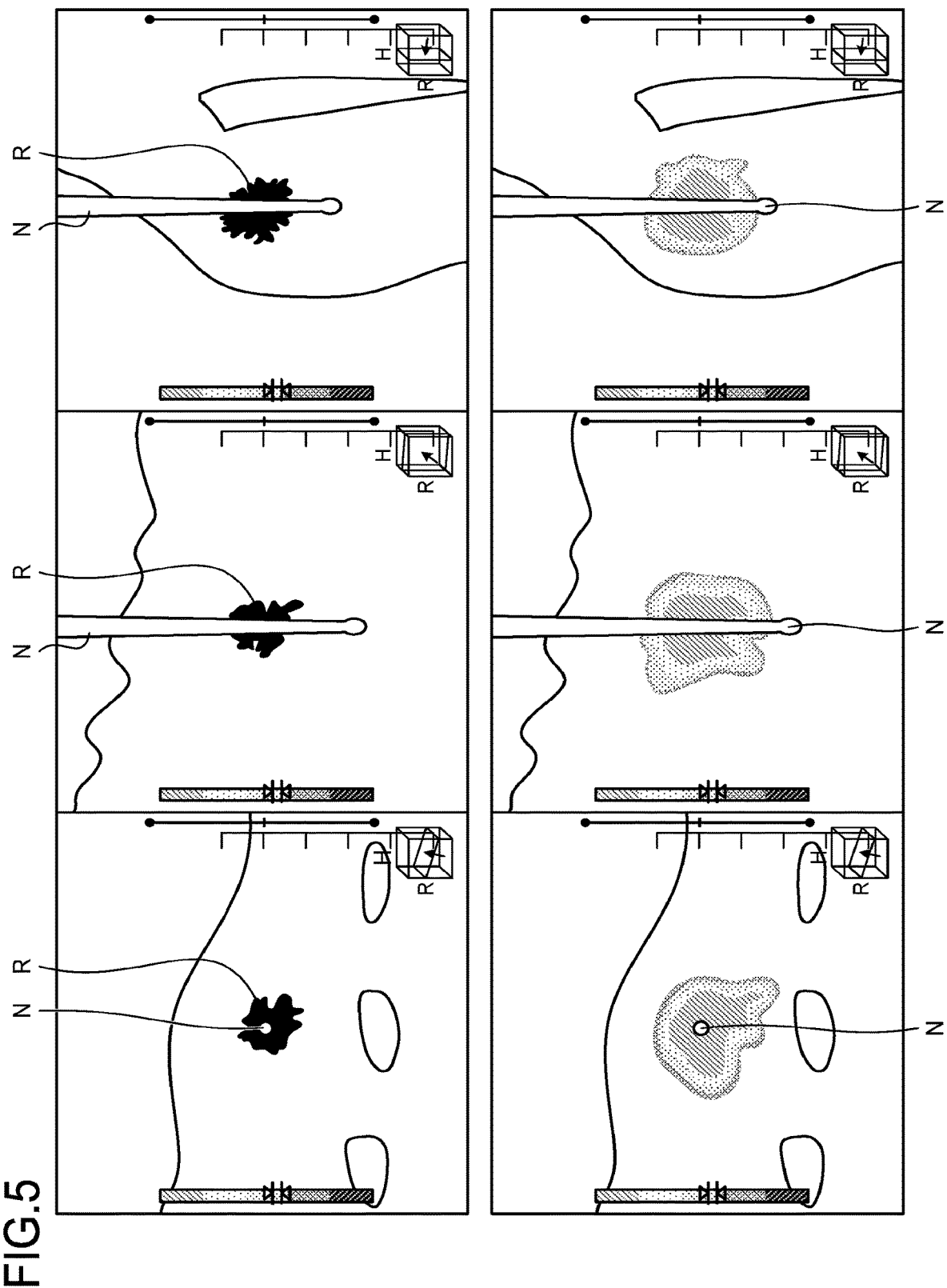
FIG. 5 is a drawing illustrating examples of display modes of temperature change maps.

FIG. 5 is a drawing illustrating other examples of display modes of the temperature change maps. In the left column of FIG. 5, a CT image on an axial cross-sectional plane is presented at the bottom, a CT image on a coronal cross-sectional plane is presented in the middle, and a CT image on a sagittal cross-sectional plane is presented at the top. Further, presented in the right column of FIG. 5 are temperature change maps each extracting only such a region that has a temperature equal to or higher than a certain level (e.g., a temperature equal to or higher than a temperature short of a target temperature by 10 degrees) and being displayed in a real-time manner so as to be superimposed on the respective CT image in the left column while using the ablation needle N or a tumor region R as a reference.

By observing the temperature change maps presented in the right column of FIG. 5, the practitioner is able to visually and promptly understand: whether or not the ablation target region has reached the target temperature; what the temperature of the ablation target region is at present; which parts of the ablation target region have not reached the target temperature; how soon the ablation target region will reach the target temperature; whether the ablation avoidance region has not reached a temperature equal to or higher than a tolerance value; what the temperature is like in the surroundings of the ablation avoidance region at present, and the like.

For example, it is possible to generate the temperature maps in the following manner: At first, the observation region prior to the ablation manipulation is imaged by the X-ray CT apparatus 1 so as to obtain a CT image serving as a reference. The CT values of the tissues in the CT image prior to the ablation correspond to temperatures approximately equal to the body temperature (approximately 36° C. to 40° C.). Subsequently, the observation region during the ablation manipulation is imaged by the X-ray CT apparatus 1 so as to obtain a CT image during the ablation. A difference image between the CT image during the ablation and the CT image prior to the ablation is generated. By using the difference value of each of the pixels, a graph indicating a correspondence relationship between CT value changes and temperature changes, and information related to temperature sensitivity of each of the tissues, it is possible to generate the temperature change map indicating how much the temperature in each of the different positions in the observation region has changed from the body temperature. The temperature change map is updated in a real-time manner, every time a CT image during the ablation is taken.

The reached temperature map is information indicating, with respect to each of the different positions in the observation region, a spatial distribution of maximum temperatures (or maximum temperature changes from a reference temperature) over a plurality of temporal phases during the ablation manipulation. The accumulated calories map is information indicating, with respect to each of the different positions in the observation region, a spatial distribution of accumulated values of temperature changes.

It is possible to generate the reached temperature map, by storing temperature changes between CT fluoroscopy temporal phases during the ablation, mapping the temperature changes in time series, and displaying the distribution (maximum temperature changes) of temporal phases having larger temperature changes from the reference level. Further, it is possible to generate the accumulated calories map by accumulating the temperature changes for each of the pixels in the observation region.

The temperature change graph is information including at least one of temperature change graphs each indicating chronological temperature changes with respect to a Region Of Interest (ROI) set in the observation region.

Figure 6:
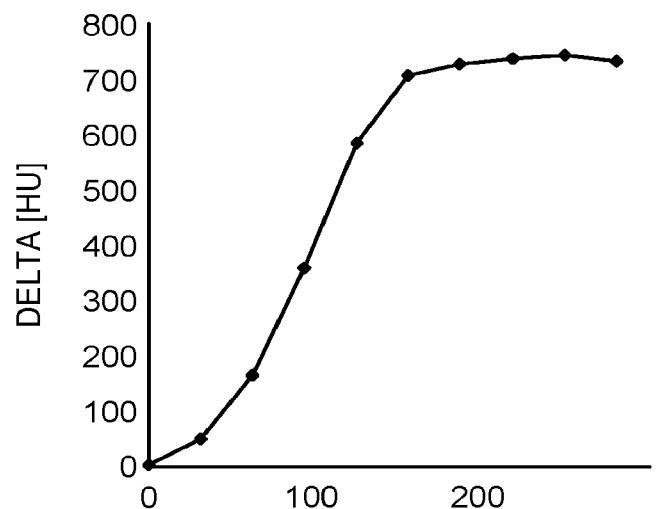
FIG. 6 is a chart illustrating an example of a temperature change graph.
Figure 7:
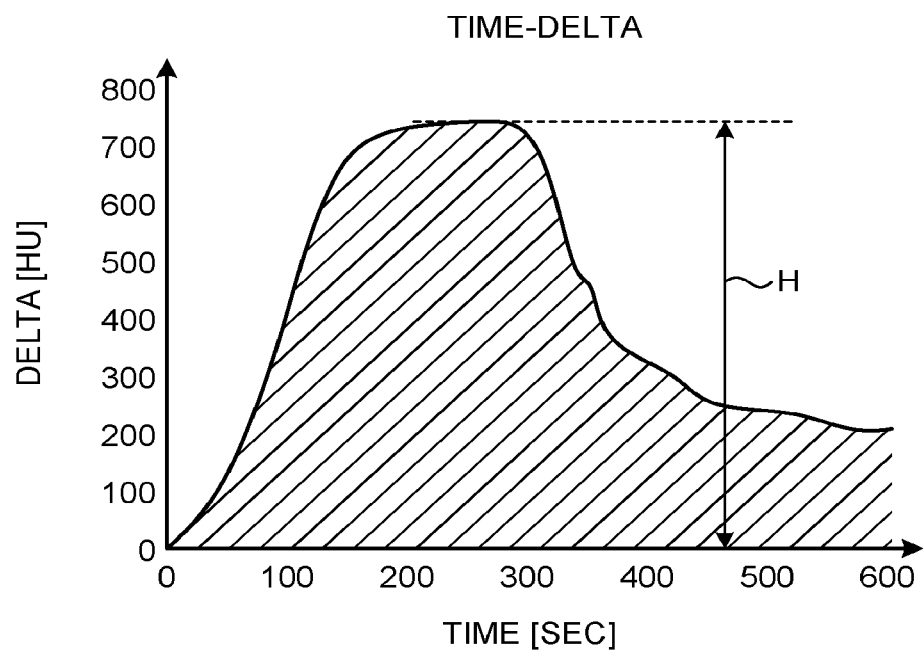
FIG. 7 is a chart illustrating another example of a temperature change graph.

FIGS. 6 and 7 are drawings illustrating examples of temperature change maps. As illustrated in FIG. 6, the temperature change graph is obtained by plotting, in a time series, representative values (e.g., average values, median values, maximum values, minimum values, etc.) of temperature changes (delta) in the ROI being set. Further, as illustrated in FIG. 7, it is possible to understand a maximum temperature change H in the ROI from the difference between the maximum value and the minimum value of the temperature change graph and an accumulated heat amount in the ROI by calculating an area below the plotted line of the temperature change graph.

The ROI used for generating the temperature change graphs may contain a plurality of pixels or may be only one pixel. Further, the ROI may be set automatically or manually. In addition, when the ROI is set automatically, a region within a predetermined radius from the surroundings of a heat generation source of the ablation needle may be set as the ROI, for example. Further, in that situation, the user may arbitrarily designate the predetermined radius.

Further, generally speaking, CT values decrease as the temperature of a tissue rises; however, in the examples in FIGS. 6 and 7, the temperature change graphs are generated by being plotted so that the CT values also increase as the temperature of the tissue rises, in consideration of intuitive understanding of the user.

Further, by employing the information generating function 150d, the processing circuit 150 is configured to judge whether or not the ablation target region has reached the target temperature and whether or not the ablation avoidance region has reached a temperature equal to or higher than the tolerance value, on the basis of the temperature change maps, the reached temperature map, the accumulated calories map, and the temperature change graphs. The judging process is realized as a result of, for example, extracting from the temperature change maps and the reached temperature map whether there is a pixel that has reached the target temperature within the ablation target region and whether there is a pixel that has reached a temperature equal to or higher than the tolerance value within the ablation avoidance region.

Further, by employing the information generating function 150d, the processing circuit 150 is configured to calculate a predicted time period until the ablation target region reaches the designated target temperature and a predicted time period until the ablation avoidance region reaches a temperature equal to or higher than the tolerance value, from a correlational expression based on the assumption that, during the treatment using the ablation device 2, the temperature changes and time are correlated with each other by using the temperature change graph regarding the region of interest.

Further, by employing the information generating function 150d, the processing circuit 150 is configured to generate the alert information on the basis of the information related to temperature. In this situation, the alert information is assistance information for attracting the practitioner's attention so that the practitioner is able to make appropriate judgments during the treatment using ablation. For example, the alert information includes at least one of the following: information to notify that the ablation target region included in the observation region has reached the target temperature (first information); information to notify that the ablation target region will reach the target temperature in a certain time period (second information); information to notify that the ablation avoidance region included in the observation region has reached the tolerance temperature (third information); information to notify that the ablation avoidance region will reach the tolerance temperature in a certain time period (fourth information); information to notify that the operations of the ablation device should be controlled (e.g., stopping the operations or changing the ablation intensity) on the basis of the information related to temperature (fifth information); information to notify that the imaging operations of the X-ray CT apparatus 1 should be controlled (e.g., stopping the operations or changing the image taking conditions) on the basis of the information related to temperature (sixth information); a predicted time period until the ablation target region reaches the target temperature (a first predicted time period); and a predicted time period until the ablation avoidance region reaches the tolerance temperature (a second predicted time period).

Typically, the alert information is image information. For example, the alert information may be an image displaying regions that have reached the target temperature and the tolerance temperature in the temperature change maps, the reached temperature map, the accumulated calories map, the temperature change graphs, or the like, with an emphasis using a different color, flashing display, or the like. Further, for example, the alert information may be an image including a message or audio stating "The ablation target region includes a part that has already reached (or exceeded) the target temperature. Please stop the ablation and the imaging immediately."; "The ablation avoidance region includes a part that has already reached (or exceeded) the tolerance temperature. Please stop the ablation and the imaging immediately."; "The ablation target region will reach the target temperature in 30 seconds."; and/or "The ablation avoidance region will reach the tolerance temperature in 30 seconds."

In this situation, the information to be included in the alert information may be selected by issuing a selection instruction through the input interface 43, for example. By employing the information generating function 150d, the processing circuit 150 is configured to generate the alert information including the selected information, on the basis of the information related to temperature.

Further, by employing the information generating function 150d and in conjunction with the generation of the alert information, the processing circuit 150 is configured to generate, on the basis of the information related to temperature, a control signal (a first control signal) for controlling the operations of the ablation device 2 (e.g., stopping the operations or changing the ablation intensity) and a control signal (a second control signal) for controlling the imaging operations of the X-ray CT apparatus 1 (e.g., stopping the operations or changing the image taking conditions). The first control signal and the second control signal both do not necessarily have to be generated; it is acceptable to generate at least one of the control signals. As for the generation of the first and the second control signals, it is possible to set priority levels as to which of the following is to be in conjunction therewith: the generation of the alert information regarding the ablation target region; and the generation of the alert information regarding the ablation avoidance region.

By employing the output controlling function 150e, the processing circuit 150 is configured to cause the display device 42 to display, in a real-time manner, the information related to temperature regarding the observation region inside the patient's body during the treatment using the ablation device 2. Further, by employing the output controlling function 150e, the processing circuit 150 is configured to cause the display device 42 to display, in a real-time manner, the temperature change map, the reached temperature map, and the accumulated calories map, together with a CT image (e.g., Multiplanar Reconstruction [MPR] images on three orthogonal cross-sectional planes) using the ablation needle or the tumor region as a reference, simultaneously (e.g., so as to be superimposed on one another or arranged side by side).

By employing the output controlling function 150e, with pre-set timing such as when the ablation target region has reached a treatment effective temperature (or a certain time period ahead of the reach) or when the ablation avoidance region has reached a temperature equal to or higher than the tolerance value (or a certain time period ahead of the reach), the processing circuit 150 is configured to cause the display device 42 to display the information related to temperature including the information that notifies the practitioner of any of these incidences.

For example, by employing the output controlling function 150e, the processing circuit 150 is configured to cause the display device 42 to display the temperature change map and/or the like in which the colors have been changed, as an alert function to notify the practitioner of any of the incidences. Further, by employing the output controlling function 150e, the processing circuit 150 causes the display device 42 to display each of the ablation target region and the ablation avoidance region with an emphasis, so as to be distinguished from the other sites.

Further, by employing the output controlling function 150e, the processing circuit 150 is configured to cause the display device 42 to display, in a real-time manner, the predicted time period until the ablation target region reaches the designated target temperature and the predicted time period until the ablation avoidance region reaches the designated tolerance temperature, during the treatment using the ablation device 2.

Further, by employing the output controlling function 150e, the processing circuit 150 is configured to cause the ablation avoidance region to be displayed with an emphasis using a color, an outline, or the like so as to be distinguished from the ablation target region and the other regions.

Further, by employing the output controlling function 150e, the processing circuit 150 is configured to cause the display device 42 to display, in a real-time manner, information related to temperature that distinguishes an already-ablated region (a target temperature reached region) from a not-yet-ablated region (a target temperature unreached region) so as to provide navigation to the next ablated position, when the ablation needle is to be newly inserted into a different position or when a new position is to be ablated, in an ablation manipulation during the treatment using the ablation device 2.

Further, by employing the output controlling function 150e, the processing circuit 150 is configured to cause the display device 42 to display, in a real-time manner, the alert information either alone or together with the information related to temperature, during the treatment using the ablation device 2. Further, by employing the output controlling function 150e, the processing circuit 150 is configured to output the first control signal used for controlling the operations of the ablation device 2 to the ablation device 2, during the treatment using the ablation device 2. Furthermore, by employing the output controlling function 150e, the processing circuit 150 is configured to output the second control signal used for controlling the imaging operations of the X-ray CT apparatus 1 to the X-ray CT apparatus 1, during the treatment using the ablation device 2.

As for the timing with which the first and the second control signals are to be output, for example, it is possible to set the timing to be any of the following: a time at which it is determined that the ablation target region included in the observation region has reached the target temperature; a time at which it is determined that the ablation avoidance region included in the observation region has reached the tolerance temperature; a time after the first predicted time period for the ablation target region to reach the target temperature has elapsed; and a time after the second predicted time period for the ablation avoidance region to reach the tolerance temperature has elapsed.

Next, a flow of operations performed by the medical image processing apparatus 100 during the treatment using the ablation device 2 will be explained.

Figure 8:
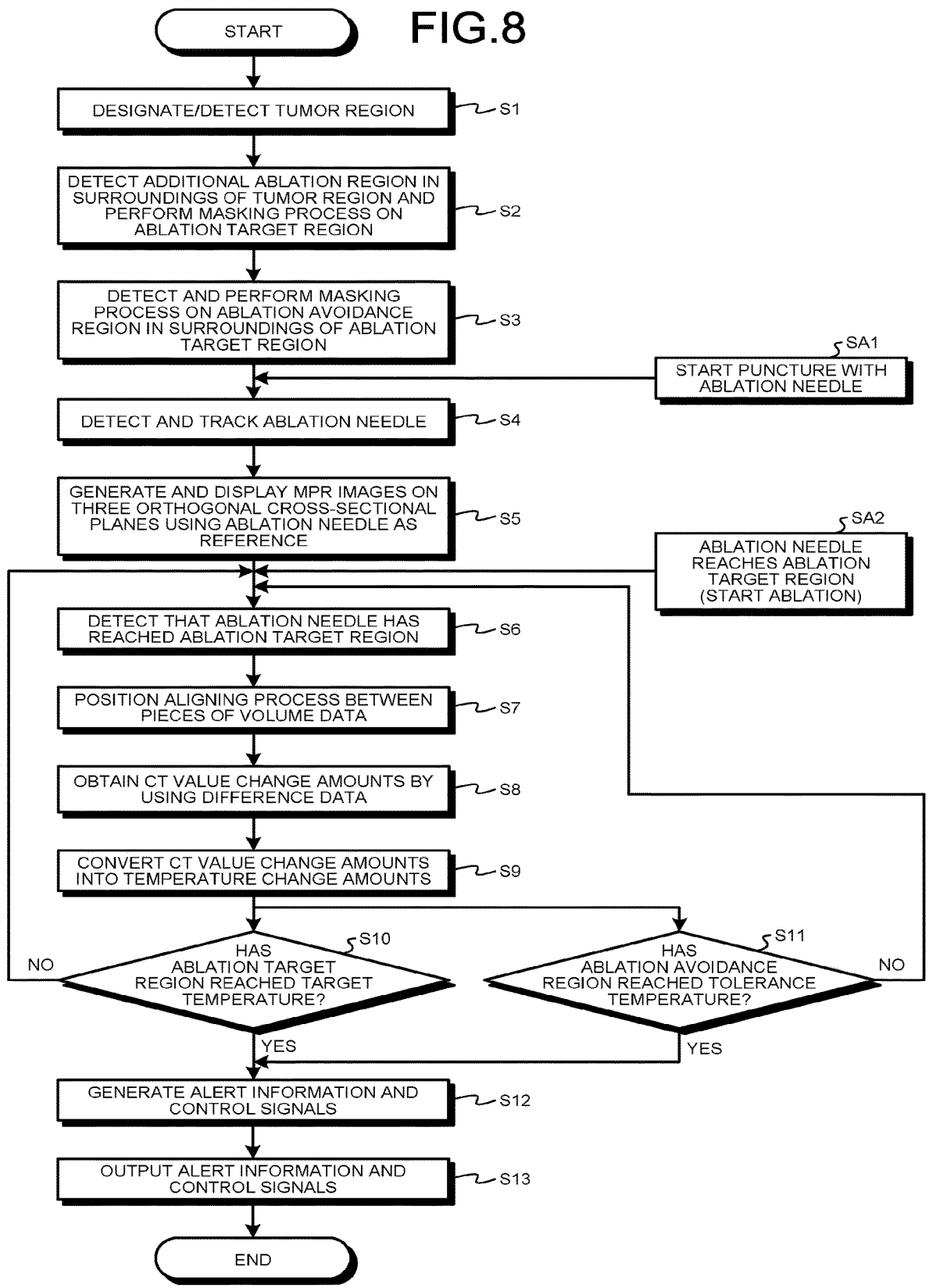
FIG. 8 is a flowchart illustrating an example of a flow of operations performed by the medical image processing apparatus according to the first embodiment during treatment using an ablation device.

FIG. 8 is a flowchart illustrating the flow of the operations performed by the medical image processing apparatus 100 during the treatment using the ablation device 2. It is assumed that, before or during the treatment using the ablation device 2, the X-ray CT apparatus 1 is configured to obtain, according to an instruction from the practitioner, volume data of the ablation target region and the ablation avoidance region from time to time by implementing CT fluoroscopy, so that the medical image processing apparatus 100 receives, in a real-time manner, the CT images obtained by the X-ray CT apparatus 1. Further, it is also assumed that, in the duration of steps S1 through S5 in FIG. 8, for example, the X-ray CT apparatus 1 is configured to obtain volume data of the observation region prior to the ablation corresponding to at least one temporal phase, by implementing CT fluoroscopy.

As illustrated in FIG. 8, at first, by employing the information generating function 150d, the processing circuit 150 designates/detects a tumor region, by using a three-dimensional image (a volume rendering image) and/or MPR images on three orthogonal cross-sectional planes obtained through the CT fluoroscopy performed by the X-ray CT apparatus 1 (step S1). The tumor region designating process may be performed on the basis of the user manually drawing on a displayed image. Alternatively, the tumor region may automatically be detected by a segmentation process. Further, the region automatically detected by the segmentation process may manually be fine-tuned by the user.

Next, by employing the information generating function 150*d*, the processing circuit 150 detects an additional ablation region in the surroundings of the tumor region having been designated or detected and further performs a masking process on the ablation target region including the tumor region and the additional ablation region (step S2). Similarly to the detection of the tumor region, the additional ablation region may be detected on the basis of manual operations of the user, may be automatically detected by a segmentation process, or may be detected by a combination of these options. Further, as a result of the masking process performed on the ablation target region, the ablation target region serving as a ROI has been set.

Subsequently, by employing the information generating function 150*d*, the processing circuit 150 detects an ablation avoidance region in the surroundings of the ablation target region and performs a masking process on the ablation avoidance region (step S3). Similarly to the detections of the tumor region and the additional ablation region, the ablation avoidance region may be detected on the basis of manual operations of the user, may be automatically detected by a segmentation process, or may be detected by a combination of these options. Further, as a result of the masking process performed on the ablation avoidance region, the ablation avoidance region serving as a ROI has been set.

After that, when the puncture of the ablation needle is started (step SA1), the processing circuit 150 detects and tracks the ablation needle by employing the information generating function 150*d* (step S4).

Subsequently, by employing the information generating function 150*d*, the processing circuit 150 generates MPR images on three orthogonal cross-sectional planes by using the ablation needle as a reference. The MPR images correspond to MPR sectional planes including the ablation needle. The MPR images may correspond to three orthogonal cross-sectional planes including the ablation needle as a basic axis. By employing the output controlling function 150*e*, the processing circuit 150 causes the display device 42 to display the generated MPR images on the three orthogonal cross-sectional planes (step S5).

After that, by employing the information generating function 150*d*, the processing circuit 150 detects that the ablation needle has reached the ablation target region (step SA2, step S6). Further, the ablation is started with arbitrary timing after the detection (step SA2).

Subsequently, by employing the information generating function 150*d*, the processing circuit 150 performs a position aligning process between pieces of chronological volume data (volume data during the ablation) received from the X-ray CT apparatus 1 after the ablation was started and the volume data prior to the ablation (step S7). The position aligning process is performed by using the position of the ablation needle or the position of the tumor region within the volume data as a reference. However, the position aligning process does not necessarily have to be performed.

After that, by employing the information generating function 150*d*, the processing circuit 150 generates difference data between the volume data during the ablation and the volume data prior to the ablation and further obtains changes in the CT values in each of the ROIs, by using the difference data (step S8).

Subsequently, by employing the information generating function 150*d*, the processing circuit 150 converts the CT value change amounts into temperature change amounts, by using changes in the CT values in observation regions, a graph indicating a correspondence relationship between CT value changes and temperature changes, and information related to temperature sensitivity of each tissue (step S9), so as to generate information related to temperature regarding each of the observation regions.

After that, by employing the information generating function 150*d*, the processing circuit 150 judges whether or not the ablation target region has reached the target temperature on the basis of the information related to temperature (step S10). By employing the information generating function 150*d*, when it is determined that the ablation target region has reached the target temperature (step S10: Yes), the processing circuit 150 generates the alert information, the first control signal, and the second control signal (step S12). On the contrary, by employing the information generating function 150*d*, when it is determined that the ablation target region has not reached the target temperature (step S10: No), the processing circuit 150 repeatedly performs the processes at steps S6 through S10.

Subsequently, by employing the information generating function 150*d*, the processing circuit 150 judges whether or not the ablation avoidance region has reached the tolerance temperature on the basis of the information related to temperature (step S11). By employing the information generating function 150*d*, when it is determined that the ablation avoidance region has reached the tolerance temperature (step S11: Yes), the processing circuit 150 generates the alert information, the first control signal, and the second control signal (step S12). On the contrary, by employing the information generating function 150*d*, when it is determined that the ablation target region has not reached the target temperature (step S11: No), the processing circuit 150 repeatedly performs the processes at steps S6 through S11.

After that, by employing the output controlling function 150*e*, the processing circuit 150 causes the display device 42 to display (output) the alert information either alone or together with the information related to temperature regarding each of the observation regions (step S13).

In this situation, for example, by employing the output controlling function 150*e*, the processing circuit 150 displays the alert information and the regions that have reached the target temperature and the tolerance temperature, with an emphasis using a different color, flashing display, or the like.

During the ablation, every time an imaging process is performed by the X-ray CT apparatus 1, the processes at steps S6 through S13 are repeatedly performed. When the ablation is completed, the information related to temperature that was generated most recently is stored in the memory 41 as manipulation execution result information and is managed for each patient.

The region that can be ablated in one session of ablation is limited to a region having a radius of a number of centimeters. Accordingly, depending on the size or the shape of the ablation target region, ablation is performed multiple times so as to ablate the entire ablation target region by inserting the ablation needle in a different position every time. Also, when a plurality of ablation target regions are set, ablation is performed multiple times by inserting the ablation needle in different positions. For each of these ablation sessions, the processes at steps S6 through S13 are repeatedly performed.

As explained above, the medical image processing apparatus according to the one embodiment includes the information generating function 150d serving as the information generating unit and the output controlling function 150e serving as the output controlling unit. The information generating function 150d is configured to generate the information related to temperature, by using the CT image obtained by imaging the one or more observation regions prior to the ablation and at least one CT image obtained by imaging the one or more observation regions during the ablation and is configured to generate the alert information on the basis of the information related to temperature. The output controlling function 150e is configured to cause the display device 42 serving as the output unit to output the alert information.

The alert information may include at least one of the following: the information to notify that the ablation target region included in the observation regions has reached the target temperature (the first information); the information to notify that the ablation target region will reach the target temperature in a certain time period (the second information); the information to notify that the ablation avoidance region included in the observation regions has reached the tolerance temperature (the third information); the information to notify that the ablation avoidance region will reach the tolerance temperature in a certain time period (the fourth information); the information to notify that the operations of the ablation device 2 should be controlled on the basis of the information related to temperature (the fifth information); and the information to notify that the imaging operations of the X-ray CT apparatus 1 should be controlled on the basis of the information related to temperature (the sixth information).

By referring to the displayed alert information, the practitioner is able to promptly and appropriately determine, during the treatment using the ablation, that the ablation by the ablation device 2 should be stopped, the imaging process by the X-ray CT apparatus 1 should be stopped, the ablation needle should be moved to a position away from the ablation avoidance region, and/or the like. As a result, it is possible to reduce unnecessary ablation and radiation exposure.

Further, the information generating function 150d is configured to generate one or both of: the first control signal to control the operations of the ablation device 2; and the second control signal to control the imaging operations of the X-ray CT apparatus 1. The output controlling function 150e is configured to transmit the first control signal to the ablation device 2. Also, the output controlling function 150e is configured to transmit the second control signal to the X-ray CT apparatus 1.

Accordingly, in conjunction with the display of the alert information, it is possible to automatically stop one or both of the ablation device 2 and the X-ray CT apparatus 1. As a result, it is possible to stop the ablation device 2 and/or the X-ray CT apparatus 1 promptly. It is therefore possible to reduce the workload of the practitioner and to reduce unnecessary ablation and radiation exposure.

Second Embodiment

Next, a medical image processing apparatus according to a second embodiment will be explained in detail. The medical image processing apparatus according to the second embodiment is configured to present information related to the temperature of a treatment target region inside a patient's body during treatment using ablation or the like, so that the presented information can be checked in a real-time manner.

The configuration of a treatment system using the medical image processing apparatus according to the second embodiment is the same as the treatment system S illustrated in FIG. 1. Further, the configuration of the medical image processing apparatus according to the second embodiment is the same as that of the medical image processing apparatus 100 illustrated in FIG. 2. Further, the configuration of an X-ray CT apparatus having built therein the medical image processing apparatus 100 according to the second embodiment is the same as that of the X-ray CT apparatus 1 illustrated in FIG. 2.

Figure 9:
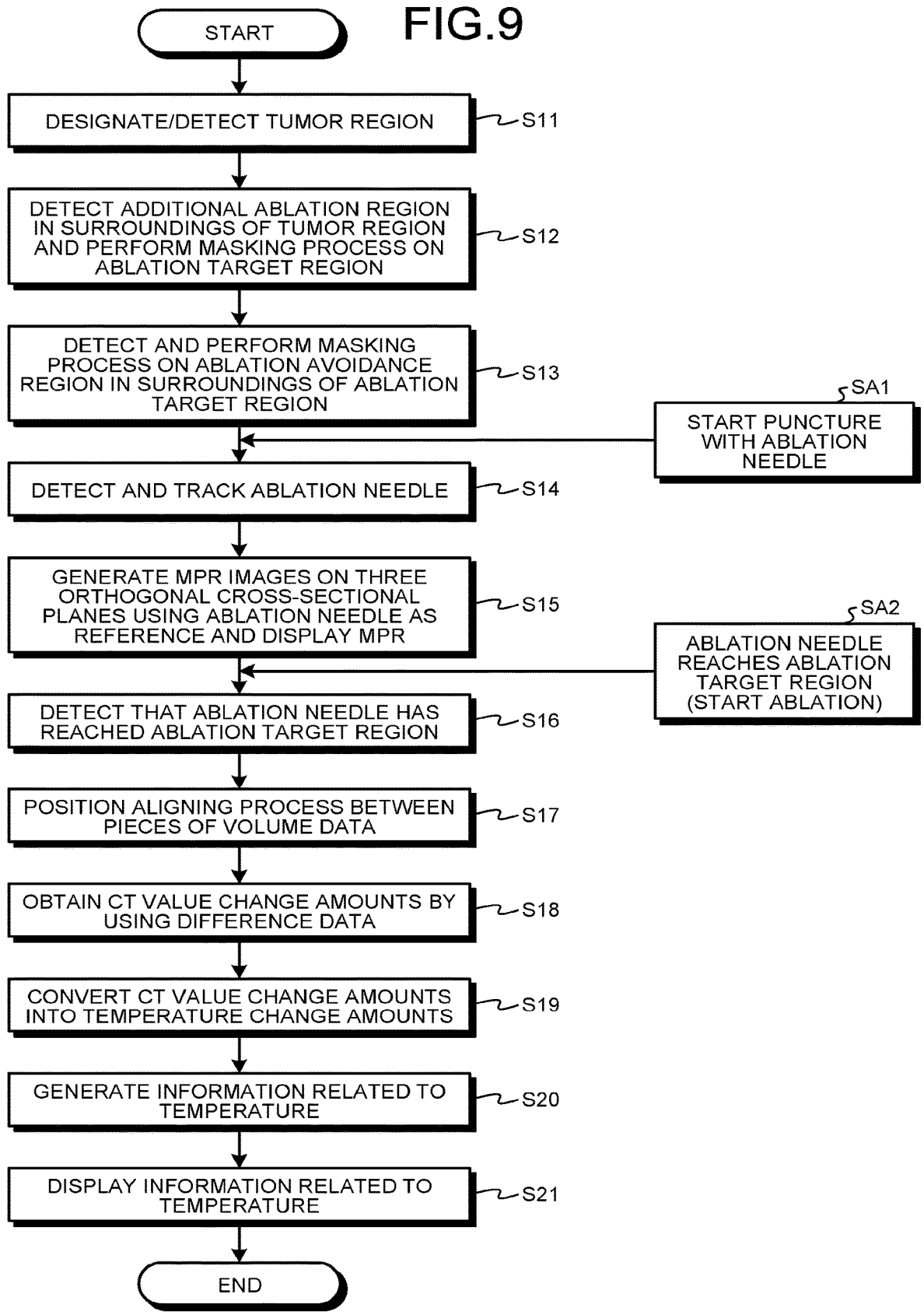
FIG. 9 is a flowchart illustrating an example of a flow of operations performed by a medical image processing apparatus according to a second embodiment during treatment using an ablation device.

FIG. 9 is a flowchart illustrating a flow of operations performed by the medical image processing apparatus 100 according to the second embodiment during treatment using the ablation device 2. Because the processes at steps S11 through S18 are the same as the processes at steps S1 through S18 illustrated in FIG. 9, explanations thereof will be omitted.

By employing the information generating function 150d, the processing circuit 150 converts the CT value change amounts into temperature change amounts, by using changes in the CT values in the observation regions, a graph indicating a correspondence relationship between CT value changes and temperature changes, and information related to temperature sensitivity of each tissue (step S19), so as to generate information related to temperature regarding each of the observation regions (step S20).

Subsequently, by employing the output controlling function 150e, the processing circuit 150 causes the display device 42 to display the information related to temperature regarding each of the observation regions (step S21).

In this situation, for example, by employing the output controlling function 150e, the processing circuit 150 causes the ablation avoidance region to be displayed with an emphasis using a color, an outline, or the like so as to be distinguished from the ablation target region and the other regions.

During the ablation, every time an imaging process is performed by the X-ray CT apparatus 1, the processes at steps S6 through S11 are repeatedly performed. When the ablation is completed, the information related to temperature that was generated most recently is stored in the memory 41 as manipulation execution result information and is managed for each patient.

The region that can be ablated in one session of ablation is limited to a region having a radius of a number of centimeters. Accordingly, depending on the size or the shape of the ablation target region, ablation is performed multiple times so as to ablate the entire ablation target region by inserting the ablation needle in a different position every time. Also, when a plurality of ablation target regions are set, ablation is performed multiple times by inserting the ablation needle in different positions.

When the ablation is performed multiple times in a single treatment procedure in this manner, it is necessary to perform the manipulation multiple times (by inserting the ablation needle multiple times). In that situation, by employing the output controlling function 150e, the processing circuit 150 retrieves and displays the manipulation execution result information of already-completed ablation processes as reference information at the time of performing an upcoming manipulation, for the purpose of helping understanding the temperature distribution state, target temperature reached regions, and target temperature unreached regions in the ablation processes up to the most recent occasion.

In other words, by employing the information generating function 150d, the processing circuit 150 reads the manipulation execution result information of the already-completed ablation processes from the memory 41 and performs a position aligning process between the manipulation execution result information and the information related to temperature at present, on the basis of the information in the surroundings of the ablation target region in each of the multiple times. Further, by employing the output controlling function 150e, the processing circuit 150 causes the display device 42 to display the information related to temperature including the manipulation execution result information resulting from the position aligning process. In this situation, for example, when the only CT fluoroscopic images that are available are MPR images on three orthogonal cross-sectional planes, it is also possible to generate and display three-dimensional data, through interpolation using the three cross-sectional planes.

When the ablation target region includes a target temperature unreached region as a result of the most recent treatment manipulation, the processing circuit 150 explicitly displays, by employing the output controlling function 150e, the target temperature unreached region by using a color different from the other regions or by using isotherms, in the information related to temperature. By using the guidance of the information related to temperature that explicitly displays the target temperature reached region and the target temperature unreached region so as to be distinguished from each other in this manner, the practitioner is able to determine an upcoming ablation position easily and accurately.

As explained above, the medical image processing apparatus according to the one embodiment includes the information generating function 150d serving as the information generating unit and the output controlling function 150e serving as the output controlling unit. The information generating function 150d is configured to generate the information related to temperature, by using the CT image obtained by imaging the one or more observation regions prior to the ablation and at least one CT image obtained by imaging the one or more observation regions during the ablation. The output controlling function 150e is configured to cause the display device 42 serving as the output unit to output the information related to temperature.

The observation regions may include the ablation target region and the ablation avoidance region. Further, the information related to temperature may include any of the following: a temperature change map indicating a spatial distribution of temperatures related to the observation regions (a first map); a reached temperature map indicating a spatial distribution of maximum temperature changes related to the observation regions (a second map); an accumulated calories map in which temperature changes related to the observation regions are accumulated (a third map); a temperature change graph indicating chronological temperature changes in a region of interest being set in the observation regions; a predicted time period until the ablation target region reaches the target temperature; and a predicted time period until the ablation avoidance region reaches the tolerance temperature.

By observing the displayed information related to temperature, the practitioner is able to perform the manipulation for the treatment while checking, in a real-time manner, an ablation status such as the temperature of the ablation target region at present, which parts of the ablation target region have reached the target temperature, how soon the ablation of the ablation target region is to be completed, and the like, as well as an avoidance status such as the temperature of the ablation avoidance region at present, whether or not the ablation avoidance region is prevented from being ablated, and the like.

Further, as a result of observing the information related to temperature, the practitioner is able to promptly and accurately address the situation by stopping the ablation, changing the position of the ablation, stopping the monitoring-purpose X-ray CT imaging process, and/or the like, in accordance with the ablation status and the avoidance status.

Furthermore, by using the guidance of the information related to temperature in which the target temperature reached region and the target temperature unreached region are displayed while being explicitly distinguished from each other, the practitioner is able to determine an upcoming ablation position easily and accurately.

As a result, during the treatment, it is possible to check, in a real-time manner, the information related to the temperature of the treatment target region inside the patient's body. It is therefore possible to improve operational efficiency during the treatment and to reduce unnecessary ablation processes and the like.

First Modification Example

Naturally, it is also possible to combine the first embodiment with the second embodiment. In that situation, for example, during treatment of ablation or the like, it is possible to check, in a real-time manner, the information related to the temperature of the treatment target region inside the patient's body. Further, by referring to the presented alert information, it is possible to promptly and appropriately determine, during the treatment using the ablation, that the ablation by the ablation device 2 should be stopped, the imaging process by the X-ray CT apparatus 1 should be stopped, the ablation needle should be moved to a position away from the ablation avoidance region, and/or the like.

Second Modification Example

In the embodiments above, the examples were explained in which the X-ray CT apparatus 1 has the functions of the medical image processing apparatus 100. Alternatively, the medical image processing apparatus 100 may be realized by using a medical workstation, a personal computer, or the like. The medical image processing apparatus 100 according to the first modification example is applicable, for example, in situations where a puncture robot is remotely operated.

Figure 10:
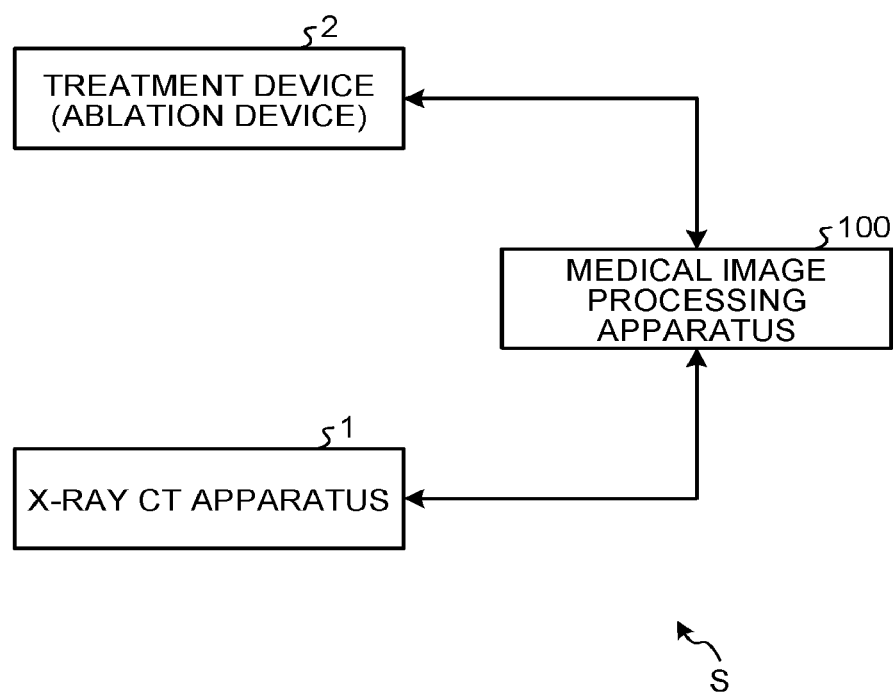
FIG. 10 is a diagram for explaining a modification example of the medical image processing apparatuses according to the embodiments.

FIG. 10 is a diagram for explaining the medical image processing apparatus 100 according to the first modification example. As illustrated in FIG. 10, the medical image processing apparatus 100 is capable of communicating with at least the X-ray CT apparatus 1. The medical image processing apparatus 100 is configured to receive, in a real-time manner, CT images taken by the X-ray CT apparatus 1 and to perform the processes described above of generating the information related to temperature, generating the alert information based on the information related to temperature, generating the first control signal, and generating the second control signal, by using the received images. The information related to temperature and the alert information are transmitted to the X-ray CT apparatus 1 and displayed in a real-time manner. Further, the first control signal is transmitted from the medical image processing apparatus 100 to the ablation device 2 in conjunction with the transmission of the alert information. The second control signal is transmitted from the medical image processing apparatus 100 to the X-ray CT apparatus 1, in conjunction with the transmission of the alert information.

Accordingly, even when the medical image processing apparatus 100 is installed in a location different from that of the ablation device 2 and the X-ray CT apparatus 1, for example, it is possible to realize the same advantageous effects as those of the embodiments.

Third Modification Example

In the embodiments described above, the examples were explained in which the medical image processing apparatus 100 is used for the ablation performed under the CT guidance of the X-ray CT apparatus 1. Alternatively, it is also possible to use the medical image processing apparatus 100 for the ablation performed under guidance of a medical image diagnosis apparatus such as a magnetic resonance imaging apparatus, an X-ray diagnosis apparatus, an ultrasound diagnosis apparatus, or the like.

Fourth Modification Example

In the first embodiment above, the example was explained in which the alert information represented by the image information is generated and displayed. Alternatively, it is also acceptable to generate alert information represented by audio information and to output the audio information from an audio output unit (a speaker).

For the audio information, for example, it is possible to adopt methods such as automatically reading a message stating "The ablation target region includes a part that has already reached (or exceeded) the target temperature. Please stop the ablation and the imaging immediately." or "The ablation avoidance region includes a part that has already reached (or exceeded) the tolerance temperature. Please stop the ablation and the imaging immediately." and/or outputting a sound that suggests stopping the ablation device 2 and/or the X-ray CT apparatus 1. Further, it is also acceptable to use the alert information represented by image information together with the alert information represented by audio information.

Fifth Modification Example

In the second embodiment above, when the treatment using the ablation is completed, the information related to temperature (e.g., the temperature change maps) obtained by the medical image processing apparatus 100 is the manipulation execution result information from which it is possible to understand the temperature distribution state of each of the regions, as a treatment result. Accordingly, it is possible to use the manipulation execution result information as reference information at the time of planning radiation treatment.

Consequently, it is desirable to configure the medical image processing apparatus 100 so as to automatically transfer the manipulation execution result information to a management server, when the treatment using the ablation is completed. With this arrangement, at the time of planning radiation treatment, it is possible to check for the target temperature unreached region and to make a treatment plan taking impacts of temperature into consideration, by retrieving and displaying the temperature distribution state with the use of the manipulation execution result information.

Sixth Modification Example

In the embodiments described above, the examples were explained in which the temperature change amounts are calculated by using the difference data between the pieces of volume data obtained by imaging the ablation target region prior to the treatment and during the treatment. However, the imaging of the ablation target region prior to the treatment is not requisite. In other words, it is also possible to obtain reference volume data corresponding to the ablation target region prior to the treatment, so as to calculate temperature change amounts by using difference data between the reference volume data and volume data obtained by imaging the ablation target region during the treatment. As for the reference volume data corresponding to the ablation target region prior to the treatment, it is possible to use, for example, data in which a reference is assigned to each of various sites classified by using an Anatomical Landmark Detection (ALD) scheme. In this situation, the reference volume data corresponding to the ablation target region prior to the treatment is an example of the reference image related to the observation region.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
   processing circuitry configured to
      set, a treatment target region, inside of a region around a heat generation source of an ablation needle with a radius designated by a user,
      receive an input to designate a treatment avoidance region positioned in surroundings of the treatment target region,
      generate information related to temperature of one or more observation regions by using a first image obtained by imaging the one or more observation regions prior to treatment and at least one second image obtained by imaging the one or more observation regions during the treatment,
      generate first alert information about the treatment target region included in the one or more observation regions and second alert information about the treatment avoidance region included in the one or more observation regions on a basis of the information related to temperature, and
      cause a display to output the treatment target region, the treatment avoidance region, the first alert information, and the second alert information together with the information related to temperature.

2. The medical image processing apparatus according to claim 1, wherein the processing circuitry is further configured to
   generate the first alert information including at least one of: first information to inform that the treatment target region included in the one or more observation regions has reached a target temperature; and second information to inform that the treatment target region will reach the target temperature in a certain time period, and generate the second alert information including at least one: third information to inform that the treatment avoidance region included in the one or more observation regions has reached a tolerance temperature; fourth information to inform that the treatment avoidance region will reach the tolerance temperature in a certain time period; fifth information to inform that an operation of a treatment device used in the treatment should be controlled, on a basis of the information related to temperature; and sixth information to inform that an imaging operation of an imaging device used for taking the first and the second images should be controlled, on the basis of the information related to temperature.

3. The medical image processing apparatus according to claim 2, wherein
the processing circuitry is further configured to generate a treatment-device control signal to control the operation of the treatment device on the basis of the information related to temperature, and cause the treatment-device control signal to be output.

4. The medical image processing apparatus according to claim 3, wherein
the processing circuitry is further configured to
generate the first alert information including a first predicted time period until the treatment target region reaches the target temperature,
generate the second alert information including a second predicted time period until the treatment avoidance region reaches the tolerance temperature, and
cause the treatment-device control signal to be output after one of the first and the second predicted time periods has elapsed.

5. The medical image processing apparatus according to claim 2, wherein
the processing circuitry is further configured to generate an imaging-device control signal to control an operation of the imaging device on a basis of the information related to temperature, and cause the imaging-device control signal to be output.

6. The medical image processing apparatus according to claim 5, wherein
the processing circuitry is further configured to
generate the first alert information including a first predicted time period until the treatment target region reaches the target temperature,
generate the second alert information including a second predicted time period until the treatment avoidance region reaches the tolerance temperature, and
cause the imaging-device control signal to be output after one of the first and the second predicted time periods has elapsed.

7. The medical image processing apparatus according to claim 2, wherein
the processing circuitry is further configured to
receive a first operation to select at least one of the first information or the second information, and a second operation to select at least one from among the third to the sixth information, and
generate the first alert information including the at least one of the first information or the second information selected by the first operation and the second alert information including the at least one from among the third to the sixth information selected by the second operation.

8. The medical image processing apparatus according to claim 1, wherein
the processing circuitry is further configured to generate the first alert information and the second alert information represented by image information, and cause the display to display the first alert information and the second alert information.

9. The medical image processing apparatus according to claim 1, wherein
the processing circuitry is further configured to generate the first alert information and the second alert information represented by audio information, and cause a speaker to output the first alert information and the second alert information.

10. The medical image processing apparatus according to claim 1, wherein
the processing circuitry is further configured to set sets the treatment target region and the treatment avoidance region as the observation regions, and generate the information related to temperature with regard to the observation regions.

11. The medical image processing apparatus according to claim 1, wherein the processing circuitry is further configured to generate the information related to temperature including at least one of: a first map indicating a spatial distribution of temperatures related to the one or more observation regions; a second map indicating a spatial distribution of maximum temperature changes related to the one or more observation regions; a third map obtained by accumulating temperature changes related to the one or more observation regions; and a graph indicating chronological temperature changes in a region of interest being set in the one or more observation regions.

12. The medical image processing apparatus according to claim 11, wherein the processing circuitry is further configured to generate each of the first, the second, and the third maps as one of: a color map in which different colors are assigned according to temperatures; and a contour line map expressing temperature differences by using isotherms.

13. The medical image processing apparatus according to claim 10, wherein the processing circuitry is further configured to generate the information related to temperature including a predicted time period until the treatment target region reaches a target temperature.

14. The medical image processing apparatus according to claim 10, wherein the processing circuitry is further configured to generate the information related to temperature including a predicted time period until the treatment avoidance region reaches a tolerance temperature.

15. The medical image processing apparatus according to claim 1, wherein, when any one of the observation regions is to be treated multiple times, the processing circuitry is further configured to generate the information related to temperature in which an already-treated region is distinguished from a not-yet-treated region.

16. The medical image processing apparatus according to claim 1, wherein the processing circuitry is further configured to cause the display to display the information related to temperature simultaneously with the second image obtained by imaging the one or more observation regions.

17. The medical image processing apparatus according to claim 16, wherein the processing circuitry is further configured to cause the display to display the information related to temperature regarding a region having temperature equal to or higher than a set value, simultaneously with the second image obtained by imaging the one or more observation regions.

18. A medical image processing apparatus comprising:
a processing circuitry configured to
set, as a treatment target region, inside of a region around a heat generation source of an ablation needle,
receive an input to designate a treatment avoidance region positioned in surroundings of the treatment target region with a radius designated by a user,
generate information related to temperature of one or more observation regions by using a reference image related to an observation region and at least one observation-region image obtained by imaging the one or more observation regions including the observation region during treatment,
generate first alert information about the treatment target region included in the one or more observation regions and second alert information about the treatment avoidance region included in the one or more observation regions on a basis of the information related to temperature, and
cause a display to output the treatment target region, the treatment avoidance region, the first alert information, and the second alert information together with the information related to temperature.

19. A medical image processing apparatus comprising:
processing circuitry configured to
set, as a treatment target region, inside of a region from region around a heat generation source of an ablation needle with a radius designated by a user,
receive an input to designate a treatment avoidance region positioned in surroundings of the treatment target region,
generate information related to temperature of one or more observation regions by using a reference image related to an observation region and at least one observation-region image obtained by imaging the one or more observation regions including the observation region during treatment,
generate first alert information about the treatment target region included in the one or more observation regions and second alert information about the treatment avoidance region included in the one or more observation regions, and
cause a display to output the treatment target region, the treatment avoidance region, the first alert information, and the second alert information together with the information related to temperature.

20. The medical image processing apparatus according to claim 1, wherein the processing circuitry is configured to
generate the information related to the temperature in each of positions of the observation region using the first image obtained by imaging the observation region including the treatment target region and the treatment avoidance region, the second image, and temperature sensitivity of each of tissues,
generate the first alert information and the second alert information based on the information related to the temperature, and
cause the display to output the treatment target region, the treatment avoidance region, the first alert information, and the second alert information together with the information related to temperature.

21. The medical image processing apparatus according to claim 1, wherein the processing circuitry is configured to cause the display to output, side by side, the second image including the treatment target region and the treatment avoidance region and an image obtained by superimposing the first alert information and the second alert information on the second image.

* * * * *